(12) United States Patent
Lichtenthaler et al.

(10) Patent No.: US 6,765,129 B1
(45) Date of Patent: Jul. 20, 2004

(54) OVEREXPRESSION OF A DNA SEQUENCE CODING FOR A 1-DESOXY-D-XYLULOSE-5-PHOSPHATE REDUCTOISOMERASE IN PLANTS

(75) Inventors: Hartmut Lichtenthaler, Karlsruhe (DE); Jörg Schwender, Pfinztal (DE); Andreas Reindl, Birkenheide (DE); Karin Herbers, Quedlinburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/959,509

(22) PCT Filed: Apr. 17, 2000

(86) PCT No.: PCT/EP00/03465

§ 371 (c)(1),
(2), (4) Date: Oct. 29, 2001

(87) PCT Pub. No.: WO00/65036

PCT Pub. Date: Nov. 2, 2000

(30) Foreign Application Priority Data

Apr. 27, 1999 (DE) .......................... 199 18 949

(51) Int. Cl.[7] ............... A01H 1/00; A01H 5/00; C12N 15/00; C12N 15/82
(52) U.S. Cl. ............ 800/282; 800/278; 800/292; 800/293; 800/294; 800/298; 536/23.1; 536/23.2; 536/23.6
(58) Field of Search ................... 800/278, 282, 800/295, 298, 292, 293, 294; 536/23.1, 23.2, 23.6; 435/183, 419, 468

(56) References Cited

U.S. PATENT DOCUMENTS 6,281,017 B1 * 8/2001 Croteau ................. 435/468

OTHER PUBLICATIONS

Accession No. AB009053 submitted Nov. 27, 1997.*
Fourgoux–Nicol et al 1999, Plant Molecular Biology 40:857–872.*
Broun P. et al. Science vol. 282; Nov. 13, 1998, pp. 1315–1317.*
Estevez J. et al. Jun. 22, 2001; vol. 276; No. 25, pp. 22901–22909.*
Rodriguez M. et al. The Plant Journal, 2001, vol. 27; No. 3, pp. 213–222.*
Shintani D. et al. Science, Dec. 11, 1998; vol. 282, pp. 2098–2100.*

* cited by examiner

Primary Examiner—David T. Fox
Assistant Examiner—Russell Kallis
(74) Attorney, Agent, or Firm—Keil & Weinkauf

(57) ABSTRACT

The invention relates to a method for producing plants containing increased quantities of tocopherols, vitamin K, carotinoids, chlorophylls and polyterpenes by overexpression of a DXPRI gene.

6 Claims, 5 Drawing Sheets

Schematic overview of the prenyl lipid metabolism

Figure 2

Nucleotide sequence of *Arabidopsis thaliana* DXPRI

```
GCGCCTCGTCAATCTTGGGATGGACCAAAACCCATCTCTATCGTTGGATCTACTGGTTCTATTGG
CACTCAGACATTGGATATTGTGGCTGAGAATCCTGACAAATTCAGAGTTGTGGCTCTAGCTGCTG
GTTCGAATGTTACTCTACTTGCTGATCAGGTAAGGAGATTTAAGCCTGCATTGGTTGCTGTTAGA
AACGAGTCACTGATTAATGAGCTTAAAGAGGCTTTAGCTGATTTGGACTATAAACTCGAGATTAT
TCCAGGAGAGCAAGGAGTGATTGAGGTTGCCCGACATCCCGAAGCTGTAACCGTTGTTACCGGAA
TAGTAGGTTGTGCGGGACTAAAGCCTACGGTTGCTGCAATTGAAGCAGGAAAGGACATTGCTCTT
GCAAACAAAGAGACATTAATCGCAGGTGGTCCTTTCGTGCTTCCGCTTGCCAACAAACATAATGT
AAAGATTCTTCCGGCAGATTCAGAACATTCTGCCATATTTCAGTGTATTCAAGGTTTGCCTGAAG
GCGCTCTGCGCAAGATAATCTTGACTGCATCTGGTGGAGCTTTTAGGGATTGGCCTGTCGAAAAG
CTAAAGGAAGTTAAAGTAGCGGATGCGTTGAAGCATCCAAACTGGAACATGGGAAAGAAAATCAC
TGTGGACTCTGCTACGCTTTTCAACAAGGGTCTTGAGGTCATTGAAGCGCATTATTTGTTTGGAG
CTGAGTATGACGATATAGAGATTGTCATTCATCCGCAAAGTATCATACATTCCATGATTGAAACA
CAGGATTCATCTGTGCTTGCTCAATTGGGTTGGCCTGATATGCGTTTACCGATTCTCTACACCAT
GTCATGGCCCGATAGAGTTCCTTGTTCTGAAGTAACTTGGCCAAGACTTGACCTTTGCAAACTCG
GTTCATTGACTTTCAAGAAACCAGACAATGTGAAATACCCATCCATGGATCTTGCTTATGCTGCT
GGACGAGCTGGAGGCACAATGACTGGAGTTCTCAGCGCCGCCAATGAGAAAGCTGTTGAAATGTT
CATTGATGAAAAGATAAGCTATTTGGATATCTTCAAGGTTGTGGAATTAACATGCGATAAACATC
GAAACGAGTTGGTAACATCACCGTCTCTTGAAGAGATTGTTCACTATGACTTGTGGGCACGTGAA
TATGCCGCGAATGTGCAGCTTTCTTCTGGTGCTAGGCCAGTTCATGCATGA
```

Figure 3

Nucleotide sequence of *Arabidopsis thaliana* DXPRI as fusion sequence

```
   1 ATGGCTAGCATGACTGGTGGACAGCAAATGGGTCGGGATCCGGCGCCTCG
  51 TCAATCTTGGGATGGACCAAAACCCATCTCTATCGTTGGATCTACTGGTT
 101 CTATTGGCACTCAGACATTGGATATTGTGGCTGAGAATCCTGACAAATTC
 151 AGAGTTGTGGCTCTAGCTGCTGGTTCGAATGTTACTCTACTTGCTGATCA
 201 GGTAAGGAGATTTAAGCCTGCATTGGTTGCTGTTAGAAACGAGTCACTGA
 251 TTAATGAGCTTAAAGAGGCTTTAGCTGATTTGGACTATAAACTCGAGATT
 301 ATTCCAGGAGAGCAAGGAGTGATTGAGGTTGCCCGACATCCCGAAGCTGT
 351 AACCGTTGTTACCGGAATAGTAGGTTGTGCGGGACTAAAGCCTACGGTTG
 401 CTGCAATTGAAGCAGGAAAGGACATTGCTCTTGCAAACAAAGAGACATTA
 451 ATCGCAGGTGGTCCTTTCGTGCTTCCGCTTGCCAACAAACATAATGTAAA
 501 GATTCTTCCGGCAGATTCAGAACATTCTGCCATATTTCAGTGTATTCAAG
 551 GTTTGCCTGAAGGCGCTCTGCGCAAGATAATCTTGACTGCATCTGGTGGA
 601 GCTTTTAGGGATTGGCCTGTCGAAAAGCTAAAGGAAGTTAAAGTAGCGGA
 651 TGCGTTGAAGCATCCAAACTGGAACATGGGAAAGAAAATCACTGTGGACT
 701 CTGCTACGCTTTTCAACAAGGGTCTTGAGGTCATTGAAGCGCATTATTTG
 751 TTTGGAGCTGAGTATGACGATATAGAGATTGTCATTCATCCGCAAAGTAT
 801 CATACATTCCATGATTGAAACACAGGATTCATCTGTGCTTGCTCAATTGG
 851 GTTGGCCTGATATGCGTTTACCGATTCTCTACACCATGTCATGGCCCGAT
 901 AGAGTTCCTTGTTCTGAAGTAACTTGGCCAAGACTTGACCTTTGCAAACT
 951 CGGTTCATTGACTTTCAAGAAACCAGACAATGTGAAATACCCATCCATGG
1001 ATCTTGCTTATGCTGCTGGACGAGCTGGAGGCACAATGACTGGAGTTCTC
1051 AGCGCCGCCAATGAGAAAGCTGTTGAAATGTTCATTGATGAAAAGATAAG
1101 CTATTTGGATATCTTCAAGGTTGTGGAATTAACATGCGATAAACATCGAA
1151 ACGAGTTGGTAACATCACCGTCTCTTGAAGAGATTGTTCACTATGACTTG
1201 TGGCACGTGAATATGCCGCGAATGTGCAGCTTTCTTCTGGTGCTAGGCC
1251 AGTTCATGCATGAAGAATTGGTTGTTGGAAGAAGAATTC
```

Binary vector for the overexpression of the *Arabidopsis thaliana* DXPRI gene in the plastid of transgenic plants Binary vector for the antisense expression of the *Arabidopsis thaliana* DXPRI gene in the plastid of transgenic plants Demonstration of the inhibition by fosmidomycin and cofactor requirement of DXPRI:

Effect of fosmidomycin on pigment neogenesis in etiolated barley seedlings

| | Chlorophylls µg / g DW or inhibition in % | | Carotenoids µg / g DW or inhibition in % | | Pigment ratios | |
|---|---|---|---|---|---|---|
| | | | | | a/b | (a+b)/(x+c) |
| Fosmido-mycin control | 4361 | (0 %) | 603 | (0 %) | 3.65 | 7.2 |
| $10^{-6}$ M | 4201 | (4 %) | 552 | (8 %) | 3.59 | 7.6 |
| $10^{-5}$ M | 2747 | (37 %) | 179 | (70 %) | 4.74 | 15.3 |
| $10^{-4}$ M | 428 | (91 %) | 0 | (100 %) | 12.32 | |

Heterologous expression of Arabidopsis thaliana DXPRI in E. coli

OVEREXPRESSION OF A DNA SEQUENCE CODING FOR A 1-DESOXY-D-XYLULOSE-5-PHOSPHATE REDUCTOISOMERASE IN PLANTS

The invention relates to a DNA encoding a polypeptide with 1-deoxy-D-xylulose-5-phosphate reductoisomerase (DXPRI) activity which originates from plants. In addition, the invention relates to the use of DNA sequences encoding a polypeptide with DXPRI activity which originates from plants for the generation of plants with an elevated tocopherol, carotenoid, vitamin K, chlorophyll and polyterpene content, specifically to the use of the DNA sequence SEQ ID No. 1 or of DNA sequences hybridizing herewith, to a method for the generation of plants with an elevated tocopherol, carotenoid, vitamin K, chlorophyll and polyterpene content, and to the resulting plant itself.

The generation of plants with an elevated sugar, enzyme and amino acid content has hitherto been an important objective in plant molecular genetics. The development of plants with an elevated vitamin content, such as, for example, an elevated tocopherol content, is, however, also of economic interest.

The naturally occurring eight compounds with vitamin E activity are derivatives of 6-chromanol (Ullmann's Encyclopedia of Industrial Chemistry, Vol. A 27 (1996), VCH Verlagsgesellschaft, Chapter 4., 478–488, Vitamin E). The first group (1a–d) is derived from tocopherol, while the second group is composed of tocotrienol derivatives (2a–d):

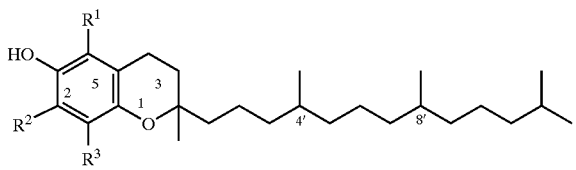

1a, α-tocopherol: $R^1=R^2=R^3=CH_3$
1b, β-tocopherol [148-03-8]: $R^1=R^3=CH_3$, $R^2=H$
1c, γ-tocopherol [54-28-4]: $R^1=H$, $R^2=R^3=CH_3$
1d, δ-tocopherol [119-13-1]: $R^1=R^2=H$, $R^3=CH_3$

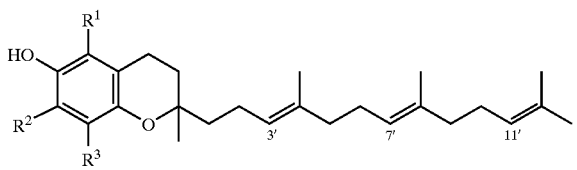

2a, α-tocotrienol [1721-51-3]: $R^1=R^2=R^3=CH_3$
2b, β-tocotrienol [490-23-3]: $R^1=R^3=CH_3$, $R^2=H$
2c, γ-tocotrienol [14101-61-2]: $R^1=H$, $R^2=R^3=CH_3$
2d, δ-tocotrienol [25612-59-3]: $R^1=R^2=H$, $R^3=CH_3$ α-Tocopherol has great economic importance.

The development of crop plants with an elevated tocopherol, vitamin K, carotenoid, chlorophyll and polyterpene content by means of tissue culture or seed mutagenesis and natural selection is set a limit. Thus, on the one hand, it must be possible to appraise, for example, the tocopherol content, or content of the desired catabolite, as early as in the tissue culture stage, and, on the other hand, only those plants whose regeneration from cell cultures to entire plants is successful can be manipulated by tissue culture techniques. Also, crop plants may show undesirable characteristics after mutagenesis and selection, and these characteristics must be reeliminated by, in some cases repeated, back crosses. Also, for example, the increase in tocopherol content would be restricted to crosses between plants of the same species.

This is why the genetic engineering approach of isolating essential biosynthesis genes which encode, for example, tocopherol synthesis performance and introducing them into crop plants in a directed fashion is superior to the traditional breeding method. Knowledge of the biosynthesis and its regulation, and identification of genes which affect biosynthesis performance, are prerequisites for this method.

Isoprenoids or terpenoids are composed of a variety of classes of lipid-soluble molecules, and they are formed partially or exclusively from $C_5$-isoprene units. Pure prenyl lipids (for example carotenoids) are composed of C skeletons based exclusively on isoprene units, while mixed prenyl lipids (for example chlorophylls, tocopherols and vitamin K), have an isoprenoid side chain linked to an aromatic nucleus.

The biosynthesis of prenyl lipids starts with 3×acetyl-CoA units which are converted into the starting isoprene unit ($C_5$), namely isopentenyl pyrophosphate (IPP), via β-hydroxymethylglutaryl-CoA (HMG-CoA) and mevalonate. Recent $C^{13}$ in vivo feeding experiments have demonstrated that the IPP formation pathway in various eubacteria, green algae and plant chloroplasts is mevalonate-independent (FIG. 1). In this pathway, hydroxyethylthiamine, which is formed by decarboxylation of pyruvate, and glycerolaldehyde-3-phosphate (3-GAP) are first converted into 1-deoxy-D-xylulose-5-phosphate in a "transketolase" reaction mediated by 1-deoxy-D-xylulose-5-phosphate synthase (DOXS) (Lange et al., 1998; Schwender et al., 1997; Arigoni et al., 1997; Lichtenthaler et al., 1997; Sprenger et al., 1997). In an intramolecular rearrangement reaction, this 1-deoxy-D-xylulose-5-phosphate is converted by DXPRI into 2-C-methyl-D-erythritol-4-phosphate and then into IPP (Arigoni et al., 1997; Zeidler et al., 1998). Biochemical data suggest that the mevalonate pathway operates in the cytosol and leads to the formation of phytosterols. The antibiotic mevinolin, a specific mevalonate formation inhibitor, only leads to sterol biosynthesis inhibition in the cytoplasma, while prenyl lipid formation in the plastids remains unaffected (Bach and Lichtenthaler, 1993). In contrast, the mevalonate-independent pathway is located in the plastids and leads predominantly to the formation of carotenoids and plastid prenyl lipids (Schwender et al., 1997; Arigoni et al., 1997).

IPP is in equilibrium with its isomer, dimethylallyl pyrophosphate (DMAPP). Condensation of IPP with DMAPP head to tail results in the monoterpene ($C_{10}$) geranylpyrophosphate (GPP). Addition of further IPP units results in the sesquiterpene ($C_{15}$) farnesyl pyrophosphate (FPP), and to the diterpene ($C_{20}$) geranylgeranyl pyrophosphate (GGPP). Bonding between two GGPP molecules results in the formation of the $C_{40}$ precursors of carotenoids.

In the case of mixed prenyl lipids, the isoprene side chain, whose length varies, is linked to non-isoprene rings such as, for example, a porphyrine ring in the case of chlorophylls a and b. The chlorophylls and phylloquinones contain a $C_{20}$ phytyl chain, in which only the first isoprene unit contains a double bond. GGPP is converted by geranylgeranyl pyrophosphate oxidoreductase (GGPPOR) to give phytyl pyrophosphate (PPP), the starting material for the subsequent formation of tocopherols.

The ring structures of the mixed prenyl lipids which lead to the formation of vitamins E and K are quinones whose starting metabolites are derived from the shikimate pathway.

The aromatic amino acids phenylalanine or tyrosine are converted into hydroxyphenyl pyruvate, which is dioxygenated to give homogentisic acid. The chorismate is formed, on the one hand, via erythrose-4-phosphate, 3'-dehydroquinate, 3'-dehydroshikimate, shikimate, shikimate-3-phosphate and 5'-enolpyruvylshikimate-3-phosphate (FIG. 1). In this process, fructose-6-phosphate and glycerolaldehyde-3-phosphate are reacted to give xylulose-5-phosphate and erythrose-4-phosphate. The above-described homogentisic acid is subsequently bonded to PPP to form the precursor of α-tocopherol and α-tocoquinone, namely 2-methyl-6-phytylquinol. Methylation steps with S-adenosylmethionine as methyl group donor lead first to 2,3-dimethyl-6-phytylquinol, subsequent cyclization leads to γ-tocopherol and further methylation to α-tocopherol (Richter, Biochemie der Pflanzen [Plant biochemistry], Georg Thieme Verlag Stuttgart, 1996).

Examples which demonstrate that manipulation of an enzyme may directionally affect metabolite flow can be found in the literature. A direct effect on the quantities of carotenoids in these transgenic tomato plants was measured in experiments on an altered expression of phytoene synthase, which links two GGPP molecules to give 15-cis-phytoene (Fray and Grierson, Plant Mol. Biol. 22(4), 589–602 (1993); Fray et al., Plant J., 8, 693–701 (1995)). As expected, transgenic tobacco plants which have reduced quantities of phenylalanine-ammonium lyase show reduced quantities of phenylpropanoid. The enzyme phenylalanine-ammonium lyase catalyzes the degradation of phenylalanine and thus withdraws it from phenylpropanoid biosynthesis (Bate et al., Proc. Natl. Acad. Sci USA 91 (16): (1994) 7608–7612; Howles et al., Plant Physiol. 112. (1996) 1617–1624).

Little is known to date on increasing the metabolite flow for elevating the tocopherol content in plants by overexpression of individual biosynthesis genes. Only WO 97/27285 describes a modification of the tocopherol content by stronger expression or down-regulation of the enzyme p-hydroxyphenylpyruvate dioxygenase (HPPD).

It is an object of the present invention to develop a transgenic plant with an elevated tocopherol, vitamin K, carotenoid, chlorophyll and polyterpene content.

We have found that this object has been achieved by overexpressing a 1-deoxy-D-xylulose-5-phosphate reductoisomerase (DXPRI) gene in the plants.

To increase the metabolite flow from the primary metabolism into the tocopherol biosynthesis, for example, the formation of 2-C-methyl-D-erythritol-4-P as essential starting substrate for all plastid isoprenoids was increased. To this end, DXPRI activity in transgenic plants was increased by overexpressing the *Arabidopsis thaliana* DXPRI gene. In principle, this can also be achieved by expressing homologous or heterologous DXPRI genes. A nucleotide sequence encoding a DXPRI was described for *E.coli* (Accession Number AB 013300; Kuzuyama et al., 1998; Takahashi et al., 1998).

Example 1 describes for the first time a plant DXPRI gene (FIG. 2, SEQ-ID No. 1) from *Arabidopsis thaliana*, which is expressed at a higher level in transgenic plants. To ensure localization in the plastids, a transit signal sequence (FIG. 3, FIG. 4) is arranged upstream of the *Arabidopsis thaliana* DXPRI nucleotide sequence. Fragment A (529 bp) in FIG. 4 contains the cauliflower mosaic virus 35S promoter (nucleotides 6909 to 7437 of the cauliflower mosaic virus). Fragment B (259 bp) contains the transketolase transit peptide. Fragment E contains the DXPRI gene. Fragment D (192 bp) contains the polyadenylation signal of gene 3 of the Ti-plasmid pTIACH5 T-DNA (Gielen et al., 1984) to terminate transcription. Another suitable expression cassette is a DNA sequence which encodes a DXPRI gene which hybridizes with a SEQ ID No. 1 and which is derived from other organisms or other plants.

The 2-C-methyl-D-erythritol-4-P, of which greater quantities are now available owing to the additional expression of the DXPRI gene, is reacted further towards tocopherols, carotenoids, vitamin K, chlorophylls and polyterpenes.

The transgenic plants are generated by transforming the plants with a construct comprising the DXPRI gene. Tobacco and oilseed rape were used as model, plants for the production of tocopherols, vitamin K, carotenoids, chlorophylls and polyterpenes.

Antisense constructs and homologous or heterologous plant DXPRI genes were transformed independently of one another into plants (FIG. 5). Fragment A (529 bp) in FIG. 5 contains the cauliflower mosaic virus 35S promoter (nucleotides 6909 to 7437 of the cauliflower mosaic virus). Fragment B (259 bp) contains the transketolase transit peptide (FIG. 3). Fragment E contains the DXPRI gene in antisense orientation. Fragment D (192 bp) contains the polyadenylation signal of gene 3 of the Ti-plasmid pTI-ACH5 T-DNA (Gielen et al., 1984) to terminate transcription. Measurements on DXPRI antisense plants showed a drastic decrease in tocopherol and carotenoid contents. This confirms the direct effect of the plastid plant DXPRI on carotenoid and tocopherol synthesis.

The invention relates to the use of the *Arabidopsis thaliana* DNA sequence SEQ ID No. 1 which encodes a DXPRI or its functional equivalents for the generation of a plant with an elevated tocopherol, carotenoid, vitamin K, chlorophyll and polyterpene content. The nucleic acid sequence may be, for example, a DNA or cDNA sequence. Encoding sequences which are suitable for insertion into an expression cassette are, for example, those which encode a DXPRI and which allow the host to overproduce tocopherols, carotenoids, vitamin K, chlorophylls and polyterpenes.

The expression cassettes also comprise regulative nucleic acid sequences which govern the expression of the encoding sequence in the host cell. In a preferred embodiment, an expression cassette comprises a promoter upstream, i.e. on the 5'-end of the encoding sequence, and a polyadenylation signal downstream, i.e. on the 3'-end, and, if appropriate, further regulatory elements which are linked operatively with the sequence in between which encodes the DXPRI gene. Operative linkage is to be understood as meaning the sequential arrangement of promoter, encoding sequence, terminator and, if appropriate, further regulatory elements in such a way that each of the regulatory elements can fulfil its function as intended when the encoding sequence is expressed. The sequences preferred for operative linkage, but not restricted thereto, are targeting sequences for guaranteeing subcellular localization in the apoplast, in the vacuole, in plastids, in the mitochondrion, in the endoplasmatic reticulum (ER), in the nucleus, in oil bodies or in other compartments, and translation enhancers such as the tobacco mosaic virus 5'-leader sequence (Gallie et al., Nucl. Acids Res. 15 (1987), 8693–8711).

As an example, the plant expression cassette can be incorporated into the tobacco transformation vector pBinAR-Hyg. FIG. 6 shows the tobacco transformation vectors pBinAR-Hyg with 35S promoter (A) and pBinAR-Hyg with the seed-specific promoter phaseolin 796 (B):

HPT: hygromycin phosphotransferase

OCS: octopin synthase terminator

PNOS: nopalin synthase promoter also shown are those restriction cleavage sites which cut the vector only once.

A suitable promoter of the expression cassette is, in principle, any promoter which is capable of governing the expression of foreign genes in plants. In particular, a plant promoter or a promoter derived from a plant virus is preferably used. Particularly preferred is the CaMV 35S promoter from cauliflower mosaic virus (Franck et al., Cell 21 (1980), 285–294). As is known, this promoter contains various recognition sequences for transcriptional effectors which in their totality lead to permanent and constitutive expression of the introduced gene (Benfey et al., EMBO J. 8 (1989), 2195–2202).

The expression cassette may also comprise a chemically inducible promoter which allows expression of the exogenous DXPRI gene in the plant to be governed at a particular point in time. Such promoters which can be used are, inter alia, for example the PRP1 promoter (Ward et al., Plant. Mol. Biol. 22 (1993), 361–366), a salicylic-acid-inducible promoter (WO 95/19443), a benzenesulfonamide-inducible promoter (EP-A 388186), a tetracyclin-inducible promoter (Gatz et al., (1992) Plant J. 2, 397–404), an abscisic-acid-inducible promoter (EP-A 335528) or an ethanol- or cyclohexanone-inducible promoter (WO 93/21334).

Furthermore, particularly preferred promoters are those which ensure expression in tissues or parts of the plant in which, for example, the biosynthesis of tocopherol or its precursors takes place. Promoters which ensure leaf-specific expression must be mentioned in particular. Promoters which must be mentioned are the potato cytosolic FBPase or the potato ST-LSI promoter (Stockhaus et al., EMBO J. 8 (1989), 2445–245).

A foreign protein was expressed stably in the seeds of transgenic tobacco plants to an extent of 0.67% of the total soluble seed protein with the aid of a seed-specific promoter (Fiedler and Conrad, Bio/Technology 10 (1995), 1090–1094). The expression cassette can therefore contain, for example, a seed-specific promoter (preferably the phaseolin promoter (U.S. Pat. No. 5,504,200), the USP promoter (Baumlein, H. et al., Mol. Gen. Genet. (1991) 225 (3), 459–467) or the LEB4 promoter (Fiedler and Conrad, 1995)), the LEB4 signal peptide, the gene to be expressed and an ER retention signal.

An expression cassette is generated by fusing a suitable promoter with a suitable DXPRI DNA sequence and, preferably, a DNA which is inserted between promoter and DXPRI DNA sequence and which encodes a chloroplast-specific transit peptide, and with a polyadenylation signal, using customary recombination and cloning techniques as they are described, for example, by T. Maniatis, E. F. Fritsch and J. Sambrook, Molecular Cloning: A Laboratory Manual, Cold Spring Harbor Laboratory, Cold Spring Harbor, N.Y. (1989) and by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley-Interscience (1987).

Particularly preferred sequences are those which ensure targeting into the apoplast, into plastids, into the vacuole, into the mitochondrion or into the endoplasmatic reticulum (ER) or which, due to a lack of suitable operative sequences, ensure that the product remains in the compartment of formation, the cytosol (Kermode, Crit. Rev. Plant Sci. 15, 4 (1996), 285–423). Localization in the ER has proved to be particularly advantageous for the amount of protein accumulation in transgenic plants (Schouten et al., Plant Mol. Biol. 30 (1996), 781–792).

Other expression cassettes which can be used are those whose DNA sequence encodes a DXPRI fusion protein, part of the fusion protein being a transit peptide which governs translocation of the polypeptide. Chloroplast-specific transit peptides which are cleaved off enzymatically from the DXPRI residue after translocation of the DXPRI gene into the chloroplasts are preferred. Particularly preferred is the transit peptide derived from plastid DXPRI or from a functional equivalent of this transit peptide (for example the transit peptide of the Rubisco small subunit or of ferredoxin NADP oxidoreductase).

Especially preferred are DNA sequences of three cassettes of the plastid transit peptide of potato plastid transketolase in three reading frames as KpnI/BamHI fragments with an ATG codon in the NcoI cleavage site:

pTP09

KpnI__GGTACCATGGCGTCTTCTTCTTCTC
TCACTCTCTCTCAAGCTATCCTCTCTCGTTCT
GTCCCTCGCCATGGCTCTGCCTCTTCTTCTC
AACTTTCCCCTTCTTCTCTCACTTTTTCCGGC
CTTAAATCCAATCCCAATATCACCACCTCCC
GCCGCCGTACTCCTTCCTCCGCCGCCGCC
GCCGCCGTCGTAAGGTCACCGGCGATTCGTG
CCTCAGCTGCAACCGAAACCATAGAGAAA
ACTGAGACTGCGGGA TCC__BamHI pTP10

KpnI__GGTACCATGGCGTCTTCTTCTTCTC
TCACTCTCTCTCAAGCTATCCTCTCTCGTTCT
GTCCCTCGCCATGGCTCTGCCTCTTCTTCTCA
ACTTTCCCCTTCTTCTCTCACTTTTTCCGGCCT
TAAATCCAATCCCAATATCACCACCTCCC
GCCGCCGTACTCCTTCCTCCGCCGCCGCCGC
CGCCGTCGTAAGGTCACCGGCGATTCGTGCCT
CAGCTGCAACCGAAACCATAGAGAAAACTGA
GACTGCGCTGGATCC__BamHI pTP11

KpnI__GGTACCATGGCGTCTTCTTCTTCTCT
CACTCTCTCTCAAGCTATCCTCTCTCGTTCTG
TCCCTCGCCATGGCTCTGCCTCTTCTTCTCA
ACTTTCCCCTTCTTCTCTCACTTTTTCCGGC
CTTAAATCCAATCCCAATATCACCACCTCCC
GCCGCCGTACTCCTTCCTCCGCCGCCGCC
GCCGCCGTCGTAAGGTCACCGGCGATTCGTGC
CTCAGCTGCAACCGAAACCATAGAGAAAA
CTGAGACTGCGGGG ATCC__BamHI

The inserted nucleotide sequence encoding a DXPRI can be prepared synthetically, obtained naturally or contain a mixture of synthetic and natural DNA constituents, and may be composed of various heterologous DXPRI gene segments of a variety of organisms. In general, synthetic nucleotide sequences are produced which are equipped with codons which are preferred by plants. These codons which are preferred by plants can be determined from codons with the highest protein frequency expressed in the plant species of the highest interest. When preparing an expression cassette, a variety of DNA fragments may be manipulated in order to obtain a nucleotide sequence which expediently reads in the correct direction and which is equipped with a correct reading frame. Adaptors or linkers may be added to the fragments in order to link the DNA fragments to each other.

The promoter and terminator regions may expediently be provided, in the direction of transcription, with a linker or polylinker containing one or more restriction sites for insertion of this sequence. As a rule, the linker has 1 to 10, in most cases 1 to 8, preferably 2 to 6, restriction sites. In general, the linker within the regulatory regions has a size less than 100 bp, frequently less than 60 bp, but at least 5 bp. The promoter may be native, or homologous, or else foreign, or heterologous, to the host plant. The expression cassette comprises, in the 5'–3' direction of transcription, the promoter, a DNA sequence encoding a DXPRI gene, and a region for transcriptional termination. Various termination regions may be exchanged for each other as desired.

Manipulations which provide suitable restriction cleavage sites or which eliminate the excess DNA or restriction cleavage sites may also be employed. In vitro mutagenesis, primer repair, restriction or ligation may be used in cases where insertions, deletions or substitutions such as, for example, transitions and transversions, are suitable. Complementary ends of the fragments may be provided for ligation in the case of suitable manipulations such as, for example, restriction, chewing back or filling in overhangs for blunt ends.

A procedure which may be of importance for the success according to the invention may be, inter alia, the attachment of the specific ER retention signal SEKDEL (Schouten, A. et al., Plant Mol. Biol. 30 (1996), 781–792), thus tripling to quadrupling the average expression level. Other retention signals which occur naturally in plant and animal proteins localized in the ER may also be employed for constructing the cassette.

Preferred polyadenylation signals are plant polyadenylation signals, preferably those which correspond essentially to *Agrobacterium tumefaciens* T-DNA-polyadenylation signals, in particular those of gene 3 of the T-DNA (octopin synthase) of the Ti-plasmid pTiACH5 (Gielen et al., EMBO J. 3 (1984), 835 et seq.), or functional equivalents.

For example, an expression cassette may comprise a constitutive promoter (preferably the CaMV 35 S promoter), the LeB4 signal peptide, the gene to be expressed, and the ER retention signal. The preferred ER retention signal used is the amino acid sequence KDEL (lysine, aspartic acid, glutamic acid, leucine).

The fused expression cassette which encodes a DXPRI gene is preferably cloned into a vector, for example pBin19, which is suitable for transforming *Agrobacterium tumefaciens*. Agrobacteria transformed with such a vector can then be used in a known manner for transforming plants, in particular crop plants, such as, for example, tobacco plants, for example by bathing wounded leaves or leaf sections in an agrobacterial suspension and subsequently growing them in suitable media. The transformation of plants by agrobacteria is known, inter alia, from F. F. White, Vectors for Gene Transfer in Higher Plants; in Transgenic Plants, Vol. 1, Engineering and Utilization, edited by S. D. Kung and R. Wu, Academic Press, 1993, pp. 15–38. Transgenic plants which comprise integrated into the expression cassette a gene for expressing a DXPRI gene can be regenerated in a known manner from the transformed cells of the wounded leaves or leaf sections.

To transform a host plant with a DNA encoding a DXPRI, an expression cassette is inserted into a recombinant vector whose vector DNA comprises additional functional regulatory signals, for example sequences for replication or integration. Suitable vectors are described, inter alia, in "Methods in Plant Molecular Biology and Biotechnology" (CRC Press), chapter 6/7, pp. 71–119 (1993).

Using the above-cited recombination and cloning techniques, the expression cassettes can be cloned into suitable vectors which allow their multiplication, for example in *E. coli*. Suitable cloning vectors are, inter alia, pBR332, pUC series, M13mp series and pACYC184. Especially suitable are binary vectors which are capable of replication in *E. coli* and in agrobacteria.

The invention furthermore relates to the use of an expression cassette comprising the DNA sequence SEQ ID No. 1, or DNA sequences hybridizing herewith, for transforming plants, plant cells, plant tissues or parts of plants. The preferred object of the use is an elevated tocopherol, vitamin K, carotenoid, chlorophyll and polyterpene content of the plant.

Depending on the choice of promoter, expression may take place specifically in the leaves, in the seeds or in other parts of the plant. Such transgenic plants, their propagation material and the cells, tissues or parts of such plants are a further subject of the present invention.

In addition, the expression cassette may also be employed for transforming bacteria, cyanobacteria, yeasts, filamentous fungi and algae for the purpose of increasing the tocopherol, vitamin K, carotenoid, chlorophyll and polyterpene content.

The transfer of foreign genes into the genome of a plant is termed transformation. It exploits the above-described methods of transforming and regenerating plants from plant tissues or plant cells for transient or stable transformation. Suitable methods are protoplast transformation by polyethylene-glycol-induced DNA uptake, the biolistic method using the gene gun—the so-called particle bombardment method, electroporation, incubation of dry embryos in DNA-containing solution, microinjection and agrobacterium-mediated gene transfer. The abovementioned methods are described in, for example, B. Jenes et al., Techniques for Gene Transfer, in: Transgenic Plants, Vol. 1, Engineering and Utilization, edited by S. D. Kung and R. Wu, Academic Press (1993), 128–143, and in Potrykus, Annu. Rev. Plant Physiol. Plant Molec. Biol. 42 (1991), 205–225). The construct to be expressed is preferably cloned into a vector which is suitable for the transformation of *Agrobacterium tumefaciens*, for example pBin19 (Bevan et al., Nucl. Acids Res. 12 (1984), 8711).

Agrobacteria transformed with an expression cassette can equally be used in a known manner for transforming plants, in particular crop plants such as cereals, corn, oats, soya, rice, cotton, sugar beet, canola, sunflower, flax, hemp, potato, tobacco, tomato, oilseed rape, alfalfa, lettuce and the various tree, nut and grapevine species, for example by bathing wounded leaves or leaf sections in an agrobacterial suspension and subsequently growing them in suitable media.

Functionally equivalent sequences which encode a DXPRI gene are those sequences which still have the desired functions, despite a differing nucleotide sequence. Functional equivalents thus encompass naturally occurring variants of the sequences described herein, and synthetic nucleotide sequences, for example those obtained by chemical synthesis and adapted to suit the codon usage of a plant.

Functional equivalents are also to be understood as meaning, in particular, natural or artificial mutations of an originally isolated sequence which encodes a DXPRI which continue to show the desired function. Mutations encompass substitutions, additions, deletions, exchanges or insertions of one or more nucleotide residues. Thus, the present invention also encompasses, for example, those nucleotide sequences which are obtained by modifying the DXPRI nucleotide sequence. The purpose of such a modification may be, for example, the further limitation of the encoding sequence contained therein or else, for example, the insertion of further restriction enzyme cleavage sites.

Functional equivalents are also those variants whose function is attenuated or increased compared with the starting gene, or gene fragment.

Also suitable are artificial DNA sequences as long as they mediate the desired characteristic, for example an elevated tocopherol content in the plant, by overexpression of the DXPRI gene in crop plants, as described above. Such artificial DNA sequences can be identified, for example, by back translation of proteins with DXPRI activity which have been constructed by means of molecular modeling, or else by in vitro selection. Especially suitable are encoding DNA sequences which have been obtained by back translating a polypeptide sequence in accordance with the host-plant-specific codon usage. An expert skilled in the art of plant genetic methods will readily be able to identify the specific codon usage by computer evaluations of other known genes of the plant to be transformed.

Further suitable equivalent nucleic acid sequences which must be mentioned are sequences which encode fusion proteins, a DXPRI polypeptide or a functionally equivalent portion of these being a constituent of the fusion protein. The second part of the fusion protein may be, for example, another enzymatically active polypeptide, or an antigenic polypeptide sequence with the aid of which detection of DXPRI expression is possible (for example myc-tag or his-tag). However, it is preferably a regulatory protein sequence such as, for example, a signal or transit peptide which leads the DXPRI protein to the desired site of action.

An elevated tocopherol, vitamin K, chlorophyll, carotenoid and polyterpene content is to be understood as meaning for the purposes of the present invention the artificially acquired capability of an increased biosynthetic performance regarding these compounds by functional overexpression of the DXPRI gene in the plant in comparison with the non-genetically-modified plant for at least one plant generation.

The tocopherol biosynthesis site, for example, is generally the leaf tissue, so that leaf-specific expression of the DXPRI gene is meaningful. However, it is obvious that tocopherol biosynthesis need not be limited to the leaf tissue but may also take place in a tissue-specific fashion in the other remaining parts of the plant, for example in fatty seeds.

The constitutive expression of the exogenous DXPRI gene is also advantageous. On the other hand, inducible expression may also be desirable.

The expression efficacy of the transgenically expressed DXPRI gene can be determined, for example, in vitro by shoot meristem propagation. In addition, altered expression of the DXPRI gene with regard to type and level, and its effect on tocopherol biosynthesis performance may be tested on test plants in greenhouse experiments.

The invention furthermore relates to transgenic plants, transformed with an expression cassette comprising the sequence SEQ ID No. 1 or DNA sequences hybridizing herewith, and to transgenic cells, tissues, parts and propagation material of such plants. Especially preferred are transgenic crop plants such as, for example, barley, wheat, rye, corn, oats, soya, rice, cotton, sugar beet, canola, sunflower, flax, hemp, potato, tobacco, tomato, oilseed rape, alfalfa, lettuce and the various tree, nut and grapevine species.

Plants for the purposes of the invention are mono- and dicotyledonous plants, or algae.

Since this biosynthetic pathway is a metabolic pathway which is exclusively located in the chloroplasts, it offers optimal target enzymes for the development of inhibitors. Since, according to current knowledge, no enzyme which is identical with, or similar to, *Arabidopsis thaliana* DXPRI is present in other higher organisms, it can be assumed that inhibitors should have a very specific action on plants. The site of action of an inhibitor, namely fosmidomycin (3-(N-formyl-N-hydroxyamino)propylphosphonic acid; Fujisawa Pharmaceutical Co.) was identified as being a DXPRI. The biochemical assay shows efficient inhibition of the enzymatic activity (FIG. 7). The following abbreviations were used in FIG. 7: DOX=1-deoxy-D-xylulose, ME=methylerythritol. The same action is found in a plant assay in which barley seedlings are subjected to fosmidomycin treatment and then examined for their chlorophyll and carotenoid content. Both substances, which are derived from precursors of the isoprenoid metabolism, are greatly reduced in terms of quantity (FIG. 8).

Overexpression of the DXPRI-encoding gene sequence SEQ ID No. 1 and SEQ ID No. 3 in a plant allows, in principle, an improved resistance to DXPRI inhibitors to be achieved. Transgenic plants generated thus are also subject-matter of the invention.

Other subject-matters of the invention are:
Methods of transforming a plant, which comprise introducing, into a plant cell, into callus tissue, an entire plant or plant protoplasts, expression cassettes comprising a DNA sequence SEQ ID No. 1 or DNA sequences hybridizing herewith.

The use of the expression cassette comprising a DNA sequence SEQ ID No. 1 or DNA sequences hybridizing herewith for generating plants with an elevated resistance to DXPRI inhibitors by stronger expression of the DNA sequence SEQ ID No. 1, or DNA sequences hybridizing herewith.

The use of the DNA sequence SEQ ID No. 1 or DNA sequences hybridizing herewith for the generation of plants with an elevated tocopherol, vitamin K, chlorophyll, carotenoid and polyterpene content by expressing a DXPRI DNA sequence in plants.

The invention is now illustrated by the examples which follow, but not limited thereto:

General Cloning Methods

The cloning steps carried out within the scope of the present invention, e.g. restriction cleavages, agarose gel electrophoresis, purification of DNA fragments, transfer of nucleic acids onto nitrocellulose and nylon membranes, linking DNA fragments, transformation of *E. coli* cells, growing bacteria, multiplying phages and sequence analysis of recombinant DNA, were carried out as described by Sambrook et al. (1989) Cold Spring Harbor Laboratory Press; ISBN 0-87969-309-6.

The bacterial strains used hereinbelow (*E. coli*, XL-I Blue) were obtained from Stratagene. The agrobacterial strain used for the transformation of plants (*Agrobacterium tumefaciens*; C58C1 with plasmid pGV2260 or pGV3850kan) was described by Deblaere et al. in Nucl. Acids Res. 13 (1985), 4777. Alternatively, the agrobacterial strain LBA4404 (Clontech) or other suitable strains may also be employed. Vectors which can be used for cloning are the vectors pUC19 (Yanish-Perron, Gene 33 (1985), 103–119) pBluescript SK- (Stratagene), pGEM-T (Promega), pZerO (Invitrogen), pBin19 (Bevan et al., Nucl. Acids Res. 12 (1984), 8711–8720) and pBinAR. (Höfgen and Willmitzer, Plant Science 66 (1990), 221–230).

Sequence Analysis of Recombinant DNA

Recombinant DNA molecules were sequenced using a laser fluorescence DNA sequencer by Licor (available from MWG Biotech, Ebersbach) following the method of Sanger (Sanger et al., Proc. Natl. Acad. Sci. USA 74 (1977), 5463–5467).

BRIEF DESCRIPTION OF THE DRAWINGS

FIG. 2. Nucleotide sequence of *Arabidopsis thaliana* DXPRI.

FIG. 3. Nucleotide sequence of *Arabidopsis thaliana* DXPRI as fusion sequence.

EXAMPLE 1

Cloning of *Arabidopsis thaliana* DXPRI

Figure 1:
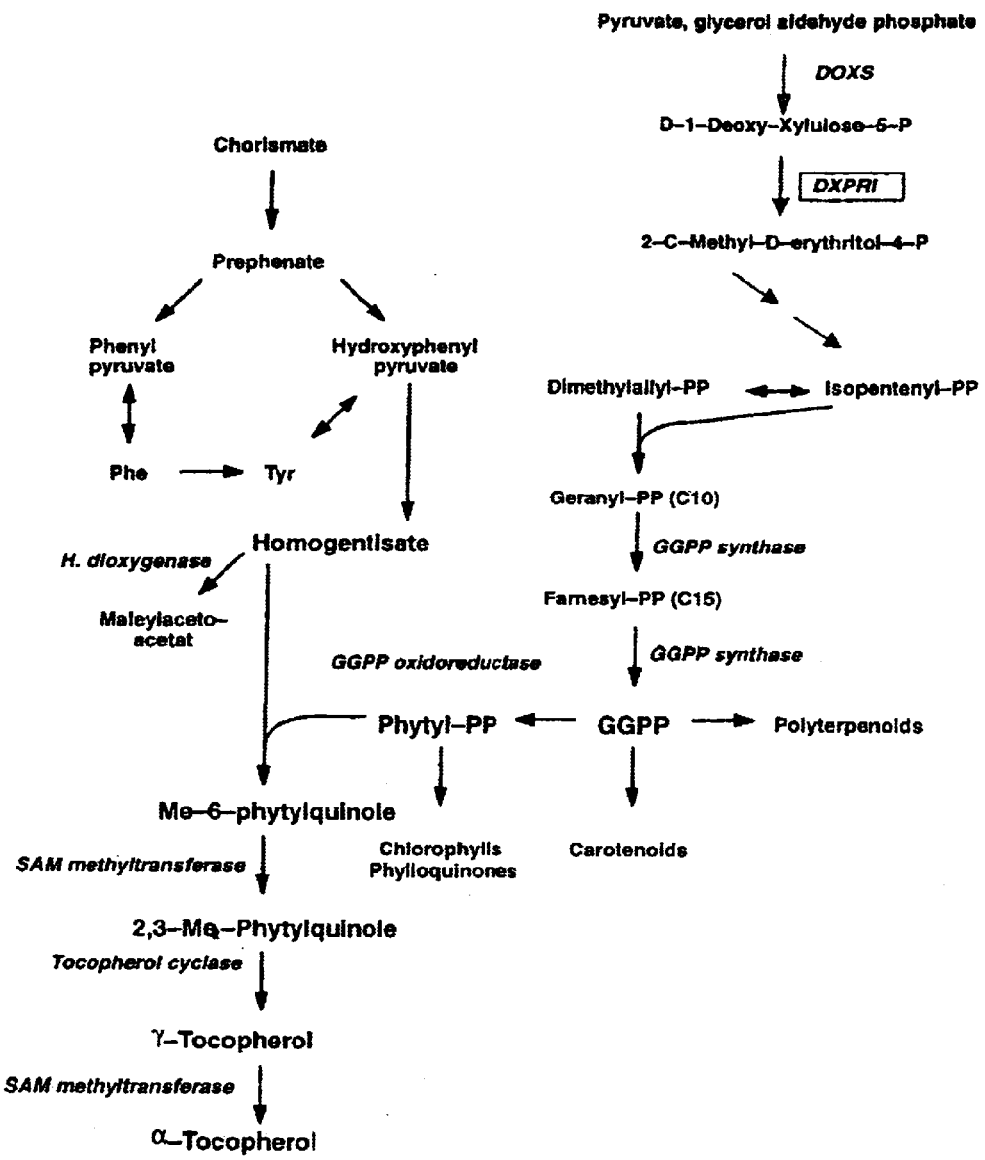
FIG. 1. Schematic overview of the prenyl lipid metabolism.

Starting from the sequence of the *E. coli* DXPRI, which had been deposited in the gene library, other bacterial protein sequences which were homologous with DXPRI were identified in gene databases. A comparison of the protein sequences, each of which only had a length of 400 amino acids, showed several conserved amino acid sequence motives. Such a motive showed homologies with a deposited genomic Arabidopsis sequence (Accession Number AB009053).

Since the bacterial DXPRI sequences show a conserved amino acid sequence close to the putative N-terminus, the beginning of a functional section of the Arabidopsis DXPRI sequence was localized very exactly in deposited genomic sequences. The C-terminal end of the sequence (stop codon) was found by comparison with the EST clone (Accession Number AA586087). A 1215 bp DXPRI fragment was cloned and studied for enzymatic functionality by means of heterologous expression.

mRNA was isolated from *Arabidopsis thaliana* (var. Columbia), and cDNA was prepared (following the instructions of the manufacturer Stratgene). PCR primers were derived from sequences AB009053 and AA586087, and with their aid a 1215 bp DNA fragment from the cDNA which had been prepared was amplified. The primer ATRv3 has a BamHI cleavage site and is chosen in such a way that, following restriction digest and ligation into pBluescript or pET5b (expression plasmid; Promega), the encoding sequence starting from the N-terminal first conserved sequence is ligated into the reading frame of the protein translation.

```
Atrv3   5' TCAGGATCCGGCGCCTCGTCAATCT 3'

Atrr1   5' GACGAATTCTTCTTCCAACAACCAATTCT 3'
```

The primers Atrv3 and Atrr1 contained a BamHI and an EcoRI cleavage site, respectively (in each case underlined).

The PCR product (Atrv3/Atrr1) was purified by means of the Gene-Clean-Kit (Dianova GmbH, Hilden) and digested with BamHI and EcoRI. For the ligation, vector pET5b was also cleaved with BamHI and EcoRI. The ligation products were transformed into *E. coli* XL1Blue (Stratagene).

Plasmid pET5bAtr contains a gene fragment encoding *Arabidopsis thaliana* DXPRI. Its sequence was determined (FIG. 2, SEQ-ID No. 1). The nucleotide sequence obtained from plasmid pEt5bAtr can be compared with sequences AB009053 and AA586087. Accordingly, the genomic sequence AB009053 contains 10 introns.

EXAMPLE 2

Cloning of the *Arabidopsis thaliana* DXPRI Into the Expression Vector pET5bAtr, and Detection of the Enzymatic Activity The expression vector pET5b (Promega) is an expression vector for the expression of recombinant proteins in *E. coli*. The plasmid is derived from pBR322 and carries a bacteriophage T7promoter for expression. For expression, the plasmid is multiplied in an *E. coli* strain which carries an inducible gene for T7 polymerase (for example JM109 (DE3); Promega). Expression of the recombinant protein is activated by inducing T7 polymerase.

pET5bAtr encodes a fusion protein which is 420 amino acids long. Amino acids 1 to 14 are derived from pET5b (fusion peptide; FIG. 3). Amino acids 15 to 420 are derived from the cloned DXPRI fragment (FIG. 2). In FIG. 3, the DNA sequence for the fusion peptide is underlined. Based on the entire sequence, the molecular weight for the protein is calculated as 45.6 kD.

The transgenic strain was incubated in the growth medium "2×YT" (per 1 l: Bacto-tryptone 16 g, yeast extract 10 g, NaCl 5 g). The cells were grown at 37° C. to an $OD_{560\ nm}$ of 0.6. After IPTG (1 MM) had been added, they were cultured for a further 10 minutes at 37° C. and then for a further 4 hours at 22° until they were harvested. The cells were centrifuged off and washed in 1% NaCl. After the cells had been disrupted (50 to 500 ml of cell culture ($OD_{560\ nm}$ of 1.0) by means of a French press, a crude protein extract was used for enzyme tests (in 4 ml of extraction buffer (Tris/HCl (pH 7.5) 100 mM, $MgCl_2$ 5 mM, DTT 2 mM, PMSF 0.1 mM). For storage, the crude extracts together with 20% of glycerol were frozen at −20° C.

Figures 8, 9:
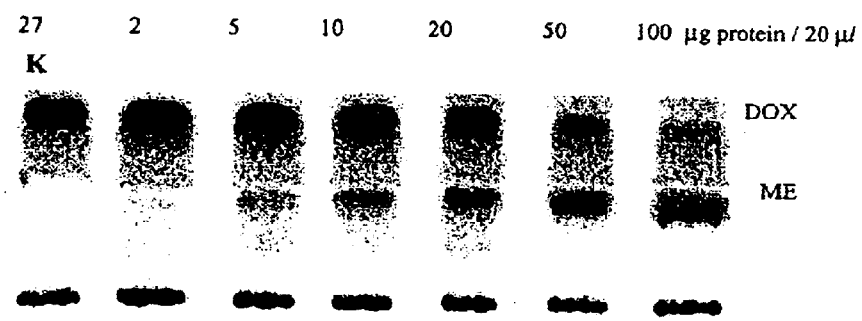
FIG. 8. Effect of fosmidomycin on pigment neogenesis in etiolated barley seedlings.
FIG. 9. Heterologous expression of *Arabidopsis thaliana* DXPRI in *E. coli*.

For the enzyme test, 15 µl (diluted to 1 to 7 mg of protein/ml) of protein extract were incubated for 30 minutes at 30° C. with $MnCl_2$ (1 mM), NaF (5 mM), $NADPH_2$ (0.5 mM) and $^{14}C$-1-deoxy-D-xylulose-5-phosphate (0.25 mM, 3 kBq). The reaction was stopped at 100° C. (30 seconds) by adding $CaCl_2$ (to 100 mM) and alkaline phosphatase (0.5 units). The product was dephosphorylated for 2 hours at 30° C. Detection was carried out by subjecting the product to separation by thin-layer chromatography on silica gel 60 (Merck) with acetone/ethyl acetate/water (50+50+2) with subsequent evaluation by Instant Imager. This gives 1-deoxy-D-xylulose (DOX; Rf 0.4) and methylerythritol (ME; Rf 0.2). FIG. 9 shows the evaluation by thin-layer chromatography and autoradiography after heterologous expression of the *Arabidopsis thaliana* DXPRI in *E. coli* and enzyme assay with the use of various total protein concentrations (µg protein/µl). K=control *E. coli* JM 109 (DE3) with plasmid pET5b without DXPRI. Samples: *E. coli* JM 109 (DE3) with plasmid pET5b with *Arabidopsis thaliana* DXPRI. The formation of ME can be inhibited efficiently by using fosmidomycin at various concentrations. This shows the mode of action of fosmidomycin as DXPRI inhibitor.

EXAMPLE 3

Preparation of the Substrate 1-deoxy-D-xylulose-5-phosphate (DOXP) for the Enzyme Assay To prepare DOXP, DOXS cloned from *Chlamydomonas reinhardtii* was used (pET5b, *E. coli* JM109(DE3)).

Enzyme extracts of IPTG-induced *E. coli* cells were incubated with [3-$^{14}$C]-pyruvate and DL-GAP. After 30 minutes, the reaction was stopped by heat-denaturation of the proteins. After centrifugation, the conversion of the radioactive pyruvate was checked by means of TLC/autoradiography, and the supernatant was used as substrate for the reductoisomerase.

DOXP as reaction product was identified with reference to the following criteria:

1. This gives rise to a radioactive product which, after treatment with alkaline phosphatase, behaves in a less polar fashion in TLC separations. This suggests that a phosphorylated product of $^{14}$C-pyruvate and GAP was formed.
2. In TLC (silica gel, acetone/ethyl acetate/water 50/50/2), the dephosphorylated product migrates in the same way as a synthetic 1-deoxy-D-xylulose sample.
   The restriction batch contained protein extract (20 µl/100 µl of batch), Tris/HCl (pH 7.5) 100 mM, DTT 2 mM, MgCl$_2$ 5 mM, Na-EDTA 500 µM, PMSF 100 µM, NaF 5 mM, TPP 1 mM, sodium pyruvate 1 mM, sodium [2-$^{14}$C]-pyruvate 20 kBq/100 µl, and DL glycerol aldehyde-3-phosphate 3.75 mM.

EXAMPLE 4

Cloning of *Arabidopsis thaliana* DXPRI Into the Plant Transformation Vector pBin19AR-TP To clone DXPRI into a binary vector, the primers were chosen in such a way that, following restriction digest and ligation into pBin19AR-TP (Promega), the encoding sequence starting from the N-terminal first conserved sequence is ligated into the reading frame of the protein translation.

```
AtrvpBin1   5' TCAGGATCCGGCGCCTCGTCAATCT 3'
AtrrpBin2   5' GACCCCGGGTTCTTCCAACAACCAATTCT 3'
```

Figure 4:
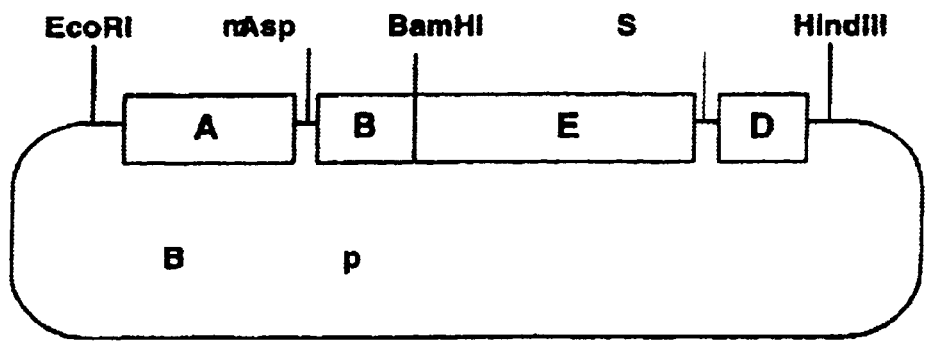
FIG. 4. Binary vector for the overexpression of the *Arabidopsis thaliana* DXPRI gene in the plastid of transgenic plants.

The primers AtrvpBin1 and AtrrpBin2 contained a BamHI or SmaI cleavage site, respectively (in each case underlined). The PCR product (AtrvpBin1/AtrrpBin2) was purified by means of the Gene-Clean-Kit (Dianova GmbH, Hilden) and digested with BamHI and SmaI. For the ligation, the vector pBin19AR-TP was also cleaved with BamHI and SmaI, and additionally contained the potato transketolase transit peptide downstream of the CaMV 35S promoter. The transit peptide ensures localization in the plastid. The construct is shown in FIG. 4.

EXAMPLE 5

Generation of DXPRI Antisense Constructs

The following primers were chosen to clone DXPRI into a binary vector in antisense orientation.

```
AtrvpBin3   5' TCACCCGGGGGCGCCTCGTCAATCT 3'
AtrrpBin4   5' GACGGATCCTTCTTCCAACAACCAATTCT 3'
```

Figure 5:
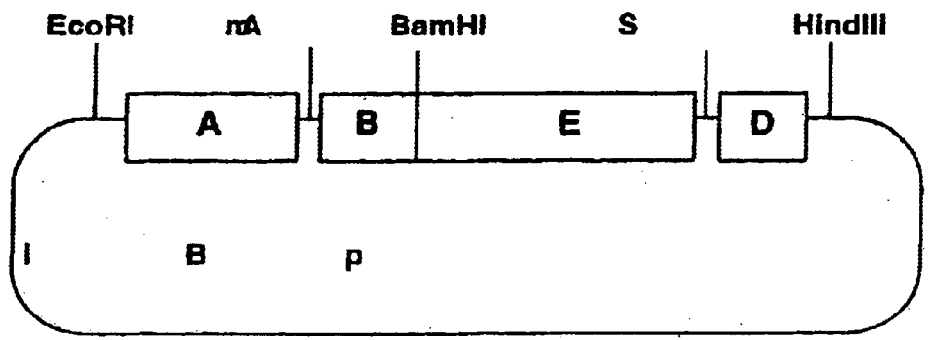
FIG. 5. Binary vector for the antisense expression of the *Arabidopsis thaliana* DXPRI gene in the plastid of transgenic plants.
Figure 6:
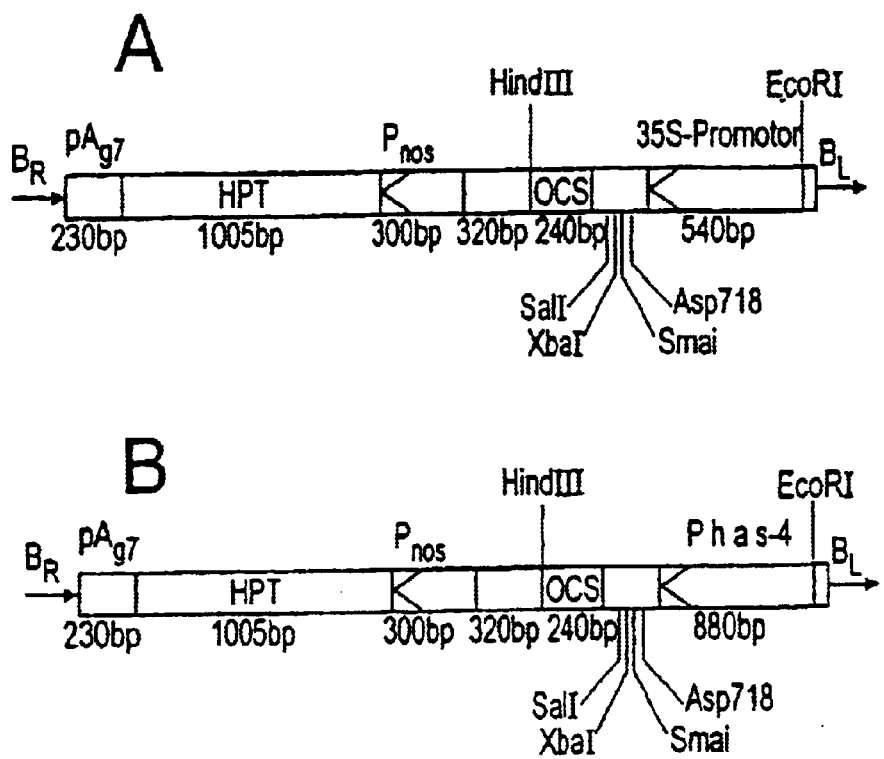
FIG. 6. Tobacco transformation vectors with 35S promoter (A) and seed specific promoter phaseolin (B).
Figure 7:
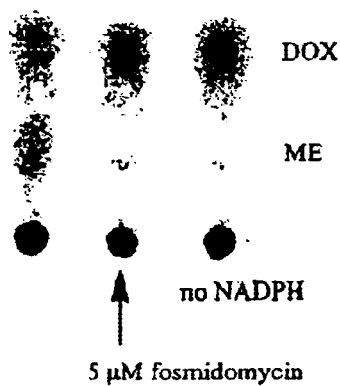
FIG. 7. Demonstration of the inhibition by fosmidomycin and cofactor requirement of DXPRI.

The primers AtrvpBin3 and AtrrpBin4 contained an SmaI or BamHI cleavage site, respectively (in each case underlined). The PCR product (AtrvpBin3/AtrrpBin4) was purified by means of the Gene-Clean-Kit (Dianova GmbH, Hilden) and digested with SmaI and BamHI. For the ligation, the vector pin19AR-TP was also cleaved with SmaI and BamHI, and additionally contained the potato transketolase transit peptide downstream of the CaMV 35S promoter. The transit peptide ensures localization in the plastid. The construct is shown in FIG. 5.

Tobacco plants with a reduced DXPRI activity were selfed and the resulting seed was harvested. To analyze the plants further, seeds from the F1 generation were used.

All antisense plants studied showed clear differences with regard to plant size. Plants were found which had the same size as the wild type, but also very small plants. The subsequent generations were, therefore, not uniform. This also applies to the reduction in DXPRI activity, which was not uniform within one line, i.e. a line cannot be defined by a specific reduction in DXPRI activity, but the lines segregate (a comparable phenomenon is shown by sedoheptulose-1,7-bisphosphatase antisense tobacco plants; cf. Harrison et al. 1998, Planta 204: 27–36).

Biomass analysis showed a correlation between reduction in DXPRI activity and biomass reduction.

EXAMPLE 6

Extraction and Detection of Tocopherol

Extraction method:
Leaf material, 100 mg fresh weight
Extraction buffer: 80% ethanol, 10 mM Hepes pH 7.0, 1 mM ascorbate
Extraction: 1:5 (w/v)
Incubation for 30 minutes at 50° C.
No centrifugation
Addition of ½ volume of n-hexane to the extract
Vortexing and centrifugation (5 minutes, room temperature)
Recovery of the deep green top phase
Repetition of the n-hexane extraction with the bottom phase
Combination of the n-hexane phases
Drying in vacuum (2–3 hours per ml of n-hexane at room temperature)
Redissolution of the residue in approx. ⅕ of the original n-hexane volume
Application of 30–50 µl onto HPLC
HPLC detection of tocopherol
Detection of fluorescence: excitation at 295 nm, emission at 330 nm
Column: RP-18 (Nucleosil 100, C18, 3 µm, Knauer)
Isocratic system: n-hexane plus 0.2% of 2-propanol
Flow rate: 0.8 ml/min (pressure: 110 bar)
Standards by Sigma or Merck
Chromatography time: 15 minutes

EXAMPLE 7

Extraction of Phenolic Substances from Leaves, and HPLC Analysis

The extraction of phenolic substances from leaves was carried out as described by Yao et al., The Plant Cell, 7 (1995), 1787.

EXAMPLE 8

Generation of Transgenic Tobacco Plants (*Nicotiana tabacum* L. cv. Samsun NN).

To generate transgenic tobacco plants with an altered prenyl lipid content, tobacco leaf disks were transformed with DXPRI sequences (SEQ ID No. 1) cloned into the transformation vector pBin19AR-TP, as described in Example 4. To transform the tobacco plants, 10 ml of an overnight culture of *Agrobacterium tumefaciens* which had grown under selection conditions was centrifuged, the supernatant was discarded, and the bacteria were resuspended in an equal volume of antibiotic-free medium. Leaf disks of sterile plants (approx. diameter 1 cm) were bathed in this bacterial suspension in a sterile Petri dish. The leaf disks were subsequently plated in Petri dishes on MS medium (Murashige and Skoog, Physiol. Plant (1962) 15, 473) supplemented with 2% sucrose and 0.8% Bacto agar. After incubation in the dark at 25° C. for two days, they were transferred to MS medium supplemented with 100 mg/l kanamycin, 500 mg/l claforan, 1 mg/l benzylaminopurin (BAP), 0.2 mg/l naphthylacetic acid (NAA), 1.6% glucose and 0.8% Bacto agar, and grown on (16 hours light/8 hours dark). Growing shoots were transferred to hormone-free MS medium supplemented with 2% sucrose, 250 mg/l claforan and 0.8% Bacto agar.

EXAMPLE 9

Generation of Transgenic Oilseed Rape Plants (*Brassica napus*)

The generation of the transgenic oilseed rape plants which have an altered prenyl lipid content followed in principle a procedure described by Bade, J. B. and Damm, B. (in Gene Transfer to Plants, Potrykus, I. and Spangenberg, G., eds, Springer Lab Manual, Springer Verlag, 1995, 30–38), which also gives the compositions of the media and buffers used.

The transformations were performed with *Agrobacterium tumefaciens* strain LBA4404 (Clontech GmbH, Heidelberg). The binary vectors used were the binary constructs which have already been described in Example 4 which comprised the *Arabidopsis thaliana* DXPRI total cDNA (SEQ ID No. 1). In all the binary vectors used here, the NOS terminator sequence was replaced by the gene 3 polyadenylation signal of Ti-plasmid pTIACH5 T-DNA (Gielen et al., 1984) for transcription termination. *Brassica napus* seeds were surface-sterilized with 70% (v/v) ethanol, washed for 10 minutes in H$_2$O at 55° C., incubated for 20 minutes in 1% strength hypochlorite solution (25% v/v Teepol, 0.1% v/v Tween 20) and washed for 20 minutes six times with sterile H$_2$O. The seeds were dried on filter paper for three days and 10–15 seeds were germinated in a glass flask containing 15 ml of germination medium. The roots and apices were removed from several seedlings (approx. length 10 cm), and the remaining hypocotyls were cut into sections approx. 6 mm in length. The approx. 600 explants thus obtained were washed for 30 minutes in 50 ml of basal medium and transferred into a 300 ml flask. After 100 ml of callus induction medium had been added, the cultures were incubated for 24 hours at 100 rpm.

An overnight culture of the agrobacterial strain was established in Luria broth medium supplemented with kanamycin (20 mg/l) at 29° C., and 2 ml of this were incubated in 50 ml of Luria broth medium without kanamycin for 4 hours at 29° C. to an OD$_{600}$ of 0.4–0.5. After the culture had been pelleted for 25 minutes at 2000 rpm, the cell pellet was resuspended in 25 ml of basal medium. The bacterial concentration in the solution was brought to an OD$_{600}$ of 0.3 by adding more basal medium.

The callus induction medium was removed from the oilseed rape explants using sterile pipettes, 50 ml of agrobacterial suspension were added, the cultures were mixed carefully and incubated for 20 minutes. The agrobacterial suspension was removed, the oilseed rape explants were washed for 1 minute with 50 ml of callus induction medium, and 100 ml of callus induction medium were subsequently added. Cocultivation was performed for 24 hours on an orbital shaker at 100 rpm. Cocultivation was stopped by removing callus induction medium, and the explants were washed twice with 25 ml of wash medium for 1 minute each time and twice for 60 minutes with 100 ml of wash medium each time, at 100 rpm. The wash medium together with the explants was transferred into 15 cm Petri dishes, and the medium was removed using sterile pipettes.

For regeneration, batches of 20–30 explants were transferred into 90 mm Petri dishes containing 25 ml of shoot induction medium supplemented with kanamycin. The Petri dishes were sealed with two layers of Leukopor and incubated at 25° C. and 2000 lux at photoperiods of 16 hours light/8 hours dark. Every 12 days, the developing calli were transferred to fresh Petri dishes containing shoot induction medium. All further steps for regenerating entire plants were carried out as described by Bade, J. B. and Damm, B. (in Gene Transfer to Plants, Potrykus, I. and Spangenberg, G., eds, Springer Lab Manual, Springer Verlag, 1995, 30–38).

EXAMPLE 10

Increasing the Tocopherol Biosynthesis in Tobacco

The overexpression of *Arabidopsis thaliana* DXPRI in tobacco was carried out as described in Example 8.

Tobacco plants which had been transformed with suitable constructs were grown in the greenhouse. The α-tocopherol content of the entire plant and of the seeds of the plant was subsequently determined. The α-tocopherol concentration was increased in all cases relative to the untransformed plant.

EXAMPLE 11

Increasing the Tocopherol Biosynthesis in Oilseed Rape

The *Arabidopsis thaliana* DXPRI cDNA (SEQ-No. 1) was provided with a CaMV35S promoter and overexpressed in oilseed rape using the 35S promoter. In parallel, the seed-specific phaseoline gene promoter was used to increase the tocopherol content specifically in the rape seed. Oil seed rape plants which had been transformed with suitable constructs were grown in the greenhouse. The α-tocopherol content of the entire plant and of the seeds of the plant was subsequently determined. The α-tocopherol concentration was increased in all cases relative to the untransformed plant.

What is claimed is:

1. Plants with an elevated tocopherol, vitamin K, carotenoid, chlorophyll and polyterpene content comprising SEQ ID NO: 1 encoding a 1-deoxy-D-xylulose-5-phosphate reductoisomerase wherein said plants are selected from the group consisting of barley, wheat, rye, corn, oats, soya, rice, cotton, sugar beet, canola, sunflower, flax, hemp, potato, tobacco, tomato, oilseed rape, alfalfa, and lettuce.

2. A method for the generation of plants with an elevated tocopherol, vitamin K, carotenoid, chlorophyll and polyterpene content, which comprises introducing and expressing, in plants, SEQ ID NO: 1.

3. A method of transforming a plant, which comprises introducing, into a plant cell, into callus tissue, an entire plant or plant cell protoplasts, an expression cassette comprising a promoter operably linked to a coding sequence comprising SEQ ID NO: 1.

4. A method of transforming plants as claimed in claim 3, wherein transformation is effected with the aid of the strain *Agrobacterium tumefaciens*, electroporation or the particle bombardment method.

5. A plant with an elevated tocopherol, vitamin K, carotenoid, chlorophyll and polyterpene content comprising an expression cassette comprising a promoter operably linked to a coding sequence comprising SEQ ID NO: 1.

6. A plant as claimed in claim 5 selected from the group consisting of soya, canola, barley, oats, wheat, oilseed rape, corn and sunflower.

* * * * *

SEQUENCE LISTING

<160> NUMBER OF SEQ ID NOS: 4

<210> SEQ ID NO 1
<211> LENGTH: 1221
<212> TYPE: DNA
<213> ORGANISM: Arabidopsis thaliana
<220> FEATURE:
<221> NAME/KEY: CDS
<222> LOCATION: (1)..(1221)

<400> SEQUENCE: 1

```
gcg cct cgt caa tct tgg gat gga cca aaa ccc atc tct atc gtt gga      48
Ala Pro Arg Gln Ser Trp Asp Gly Pro Lys Pro Ile Ser Ile Val Gly
1               5                   10                  15 tct act ggt tct att ggc act cag aca ttg gat att gtg gct gag aat      96
Ser Thr Gly Ser Ile Gly Thr Gln Thr Leu Asp Ile Val Ala Glu Asn
                20                  25                  30 cct gac aaa ttc aga gtt gtg gct cta gct gct ggt tcg aat gtt act     144
Pro Asp Lys Phe Arg Val Val Ala Leu Ala Ala Gly Ser Asn Val Thr
            35                  40                  45 cta ctt gct gat cag gta agg aga ttt aag cct gca ttg gtt gct gtt     192
Leu Leu Ala Asp Gln Val Arg Arg Phe Lys Pro Ala Leu Val Ala Val
        50                  55                  60 aga aac gag tca ctg att aat gag ctt aaa gag gct tta gct gat ttg     240
Arg Asn Glu Ser Leu Ile Asn Glu Leu Lys Glu Ala Leu Ala Asp Leu
65                  70                  75                  80 gac tat aaa ctc gag att att cca gga gag caa gga gtg att gag gtt     288
Asp Tyr Lys Leu Glu Ile Ile Pro Gly Glu Gln Gly Val Ile Glu Val
                85                  90                  95 gcc cga cat ccc gaa gct gta acc gtt gtt acc gga ata gta ggt tgt     336
Ala Arg His Pro Glu Ala Val Thr Val Val Thr Gly Ile Val Gly Cys
                100                 105                 110 gcg gga cta aag cct acg gtt gct gca att gaa gca gga aag gac att     384
Ala Gly Leu Lys Pro Thr Val Ala Ala Ile Glu Ala Gly Lys Asp Ile
            115                 120                 125 gct ctt gca aac aaa gag aca tta atc gca ggt ggt cct ttc gtg ctt     432
Ala Leu Ala Asn Lys Glu Thr Leu Ile Ala Gly Gly Pro Phe Val Leu
        130                 135                 140 ccg ctt gcc aac aaa cat aat gta aag att ctt ccg gca gat tca gaa     480
Pro Leu Ala Asn Lys His Asn Val Lys Ile Leu Pro Ala Asp Ser Glu
145                 150                 155                 160 cat tct gcc ata ttt cag tgt att caa ggt ttg cct gaa ggc gct ctg     528
His Ser Ala Ile Phe Gln Cys Ile Gln Gly Leu Pro Glu Gly Ala Leu
                165                 170                 175 cgc aag ata atc ttg act gca tct ggt gga gct ttt agg gat tgg cct     576
Arg Lys Ile Ile Leu Thr Ala Ser Gly Gly Ala Phe Arg Asp Trp Pro
            180                 185                 190 gtc gaa aag cta aag gaa gtt aaa gta gcg gat gcg ttg aag cat cca     624
Val Glu Lys Leu Lys Glu Val Lys Val Ala Asp Ala Leu Lys His Pro
        195                 200                 205 aac tgg aac atg gga aag aaa atc act gtg gac tct gct acg ctt ttc     672
Asn Trp Asn Met Gly Lys Lys Ile Thr Val Asp Ser Ala Thr Leu Phe
    210                 215                 220 aac aag ggt ctt gag gtc att gaa gcg cat tat ttg ttt gga gct gag     720
Asn Lys Gly Leu Glu Val Ile Glu Ala His Tyr Leu Phe Gly Ala Glu
225                 230                 235                 240 tat gac gat ata gag att gtc att cat ccg caa agt atc ata cat tcc     768
Tyr Asp Asp Ile Glu Ile Val Ile His Pro Gln Ser Ile Ile His Ser
                245                 250                 255
```

```
atg att gaa aca cag gat tca tct gtg ctt gct caa ttg ggt tgg cct          816
Met Ile Glu Thr Gln Asp Ser Ser Val Leu Ala Gln Leu Gly Trp Pro
        260                 265                 270 gat atg cgt tta ccg att ctc tac acc atg tca tgg ccc gat aga gtt          864
Asp Met Arg Leu Pro Ile Leu Tyr Thr Met Ser Trp Pro Asp Arg Val
            275                 280                 285 cct tgt tct gaa gta act tgg cca aga ctt gac ctt tgc aaa ctc ggt          912
Pro Cys Ser Glu Val Thr Trp Pro Arg Leu Asp Leu Cys Lys Leu Gly
    290                 295                 300 tca ttg act ttc aag aaa cca gac aat gtg aaa tac cca tcc atg gat          960
Ser Leu Thr Phe Lys Lys Pro Asp Asn Val Lys Tyr Pro Ser Met Asp
305                 310                 315                 320 ctt gct tat gct gct gga cga gct gga ggc aca atg act gga gtt ctc         1008
Leu Ala Tyr Ala Ala Gly Arg Ala Gly Gly Thr Met Thr Gly Val Leu
                325                 330                 335 agc gcc gcc aat gag aaa gct gtt gaa atg ttc att gat gaa aag ata         1056
Ser Ala Ala Asn Glu Lys Ala Val Glu Met Phe Ile Asp Glu Lys Ile
            340                 345                 350 agc tat ttg gat atc ttc aag gtt gtg gaa tta aca tgc gat aaa cat         1104
Ser Tyr Leu Asp Ile Phe Lys Val Val Glu Leu Thr Cys Asp Lys His
        355                 360                 365 cga aac gag ttg gta aca tca ccg tct ctt gaa gag att gtt cac tat         1152
Arg Asn Glu Leu Val Thr Ser Pro Ser Leu Glu Glu Ile Val His Tyr
370                 375                 380 gac ttg tgg gca cgt gaa tat gcc gcg aat gtg cag ctt tct tct ggt         1200
Asp Leu Trp Ala Arg Glu Tyr Ala Ala Asn Val Gln Leu Ser Ser Gly
385                 390                 395                 400 gct agg cca gtt cat gca tga                                             1221
Ala Arg Pro Val His Ala
                405

<210> SEQ ID NO 2
<211> LENGTH: 406
<212> TYPE: PRT
<213> ORGANISM: Arabidopsis thaliana

<400> SEQUENCE: 2

Ala Pro Arg Gln Ser Trp Asp Gly Pro Lys Pro Ile Ser Ile Val Gly
1               5                   10                  15

Ser Thr Gly Ser Ile Gly Thr Gln Thr Leu Asp Ile Val Ala Glu Asn
            20                  25                  30

Pro Asp Lys Phe Arg Val Val Ala Leu Ala Ala Gly Ser Asn Val Thr
        35                  40                  45

Leu Leu Ala Asp Gln Val Arg Arg Phe Lys Pro Ala Leu Val Ala Val
    50                  55                  60

Arg Asn Glu Ser Leu Ile Asn Glu Leu Lys Glu Ala Leu Ala Asp Leu
65                  70                  75                  80

Asp Tyr Lys Leu Glu Ile Ile Pro Gly Glu Gln Gly Val Ile Glu Val
                85                  90                  95

Ala Arg His Pro Glu Ala Val Thr Val Thr Gly Ile Val Gly Cys
            100                 105                 110

Ala Gly Leu Lys Pro Thr Val Ala Ile Glu Ala Gly Lys Asp Ile
        115                 120                 125

Ala Leu Ala Asn Lys Glu Thr Leu Ile Ala Gly Pro Phe Val Leu
    130                 135                 140

Pro Leu Ala Asn Lys His Asn Val Lys Ile Leu Pro Ala Asp Ser Glu
145                 150                 155                 160

His Ser Ala Ile Phe Gln Cys Ile Gln Gly Leu Pro Glu Gly Ala Leu
```

-continued

```
                        165                 170                 175
Arg Lys Ile Ile Leu Thr Ala Ser Gly Gly Ala Phe Arg Asp Trp Pro
                180                 185                 190
Val Glu Lys Leu Lys Glu Val Lys Val Ala Asp Ala Leu Lys His Pro
            195                 200                 205
Asn Trp Asn Met Gly Lys Lys Ile Thr Val Asp Ser Ala Thr Leu Phe
        210                 215                 220
Asn Lys Gly Leu Glu Val Ile Glu Ala His Tyr Leu Phe Gly Ala Glu
225                 230                 235                 240
Tyr Asp Asp Ile Glu Ile Val Ile His Pro Gln Ser Ile Ile His Ser
                245                 250                 255
Met Ile Glu Thr Gln Asp Ser Ser Val Leu Ala Gln Leu Gly Trp Pro
                260                 265                 270
Asp Met Arg Leu Pro Ile Leu Tyr Thr Met Ser Trp Pro Asp Arg Val
            275                 280                 285
Pro Cys Ser Glu Val Thr Trp Pro Arg Leu Asp Leu Cys Lys Leu Gly
        290                 295                 300
Ser Leu Thr Phe Lys Lys Pro Asp Asn Val Lys Tyr Pro Ser Met Asp
305                 310                 315                 320
Leu Ala Tyr Ala Ala Gly Arg Ala Gly Gly Thr Met Thr Gly Val Leu
                325                 330                 335
Ser Ala Ala Asn Glu Lys Ala Val Glu Met Phe Ile Asp Glu Lys Ile
                340                 345                 350
Ser Tyr Leu Asp Ile Phe Lys Val Val Glu Leu Thr Cys Asp Lys His
            355                 360                 365
Arg Asn Glu Leu Val Thr Ser Pro Ser Leu Glu Glu Ile Val His Tyr
        370                 375                 380
Asp Leu Trp Ala Arg Glu Tyr Ala Ala Asn Val Gln Leu Ser Ser Gly
385                 390                 395                 400
Ala Arg Pro Val His Ala
                405

<210> SEQ ID NO 3
<211> LENGTH: 1289
<212> TYPE: DNA
<213> ORGANISM: Arabidopsis thaliana
<220> FEATURE:
<221> NAME/KEY: CDS
<222> LOCATION: (1)..(1263)

<400> SEQUENCE: 3 atg gct agc atg act ggt gga cag caa atg ggt cgg gat ccg gcg cct      48
Met Ala Ser Met Thr Gly Gly Gln Gln Met Gly Arg Asp Pro Ala Pro
1               5                  10                  15 cgt caa tct tgg gat gga cca aaa ccc atc tct atc gtt gga tct act      96
Arg Gln Ser Trp Asp Gly Pro Lys Pro Ile Ser Ile Val Gly Ser Thr
            20                  25                  30 ggt tct att ggc act cag aca ttg gat att gtg gct gag aat cct gac     144
Gly Ser Ile Gly Thr Gln Thr Leu Asp Ile Val Ala Glu Asn Pro Asp
        35                  40                  45 aaa ttc aga gtt gtg gct cta gct gct ggt tcg aat gtt act cta ctt     192
Lys Phe Arg Val Val Ala Leu Ala Ala Gly Ser Asn Val Thr Leu Leu
    50                  55                  60 gct gat cag gta agg aga ttt aag cct gca ttg gtt gct gtt aga aac     240
Ala Asp Gln Val Arg Arg Phe Lys Pro Ala Leu Val Ala Val Arg Asn
65                  70                  75                  80 gag tca ctg att aat gag ctt aaa gag gct tta gct gat ttg gac tat     288
```

```
                                                    -continued

Glu Ser Leu Ile Asn Glu Leu Lys Glu Ala Leu Ala Asp Leu Asp Tyr
                    85                  90                  95 aaa ctc gag att att cca gga gag caa gga gtg att gag gtt gcc cga         336
Lys Leu Glu Ile Ile Pro Gly Glu Gln Gly Val Ile Glu Val Ala Arg
                100                 105                 110 cat ccc gaa gct gta acc gtt gtt acc gga ata gta ggt tgt gcg gga         384
His Pro Glu Ala Val Thr Val Val Thr Gly Ile Val Gly Cys Ala Gly
                115                 120                 125 cta aag cct acg gtt gct gca att gaa gca gga aag gac att gct ctt         432
Leu Lys Pro Thr Val Ala Ala Ile Glu Ala Gly Lys Asp Ile Ala Leu
            130                 135                 140 gca aac aaa gag aca tta atc gca ggt ggt cct ttc gtg ctt ccg ctt         480
Ala Asn Lys Glu Thr Leu Ile Ala Gly Gly Pro Phe Val Leu Pro Leu
145                 150                 155                 160 gcc aac aaa cat aat gta aag att ctt ccg gca gat tca gaa cat tct         528
Ala Asn Lys His Asn Val Lys Ile Leu Pro Ala Asp Ser Glu His Ser
                165                 170                 175 gcc ata ttt cag tgt att caa ggt ttg cct gaa ggc gct ctg cgc aag         576
Ala Ile Phe Gln Cys Ile Gln Gly Leu Pro Glu Gly Ala Leu Arg Lys
                180                 185                 190 ata atc ttg act gca tct ggt gga gct ttt agg gat tgg cct gtc gaa         624
Ile Ile Leu Thr Ala Ser Gly Gly Ala Phe Arg Asp Trp Pro Val Glu
                195                 200                 205 aag cta aag gaa gtt aaa gta gcg gat gcg ttg aag cat cca aac tgg         672
Lys Leu Lys Glu Val Lys Val Ala Asp Ala Leu Lys His Pro Asn Trp
        210                 215                 220 aac atg gga aag aaa atc act gtg gac tct gct acg ctt ttc aac aag         720
Asn Met Gly Lys Lys Ile Thr Val Asp Ser Ala Thr Leu Phe Asn Lys
225                 230                 235                 240 ggt ctt gag gtc att gaa gcg cat tat ttg ttt gga gct gag tat gac         768
Gly Leu Glu Val Ile Glu Ala His Tyr Leu Phe Gly Ala Glu Tyr Asp
                245                 250                 255 gat ata gag att gtc att cat ccg caa agt atc ata cat tcc atg att         816
Asp Ile Glu Ile Val Ile His Pro Gln Ser Ile Ile His Ser Met Ile
                260                 265                 270 gaa aca cag gat tca tct gtg ctt gct caa ttg ggt tgg cct gat atg         864
Glu Thr Gln Asp Ser Ser Val Leu Ala Gln Leu Gly Trp Pro Asp Met
            275                 280                 285 cgt tta ccg att ctc tac acc atg tca tgg ccc gat aga gtt cct tgt         912
Arg Leu Pro Ile Leu Tyr Thr Met Ser Trp Pro Asp Arg Val Pro Cys
            290                 295                 300 tct gaa gta act tgg cca aga ctt gac ctt tgc aaa ctc ggt tca ttg         960
Ser Glu Val Thr Trp Pro Arg Leu Asp Leu Cys Lys Leu Gly Ser Leu
305                 310                 315                 320 act ttc aag aaa cca gac aat gtg aaa tac cca tcc atg gat ctt gct        1008
Thr Phe Lys Lys Pro Asp Asn Val Lys Tyr Pro Ser Met Asp Leu Ala
                325                 330                 335 tat gct gct gga cga gct gga ggc aca atg act gga gtt ctc agc gcc        1056
Tyr Ala Ala Gly Arg Ala Gly Gly Thr Met Thr Gly Val Leu Ser Ala
                340                 345                 350 gcc aat gag aaa gct gtt gaa atg ttc att gat gaa aag ata agc tat        1104
Ala Asn Glu Lys Ala Val Glu Met Phe Ile Asp Glu Lys Ile Ser Tyr
            355                 360                 365 ttg gat atc ttc aag gtt gtg gaa tta aca tgc gat aaa cat cga aac        1152
Leu Asp Ile Phe Lys Val Val Glu Leu Thr Cys Asp Lys His Arg Asn
            370                 375                 380 gag ttg gta aca tca ccg tct ctt gaa gag att gtt cac tat gac ttg        1200
Glu Leu Val Thr Ser Pro Ser Leu Glu Glu Ile Val His Tyr Asp Leu
385                 390                 395                 400
```

```
tgg gca cgt gaa tat gcc gcg aat gtg cag ctt tct tct ggt gct agg      1248
Trp Ala Arg Glu Tyr Ala Ala Asn Val Gln Leu Ser Ser Gly Ala Arg
            405                 410                 415 cca gtt cat gca tga agaattggtt gttggaagaa gaattc                      1289
Pro Val His Ala
        420
```

<210> SEQ ID NO 4
<211> LENGTH: 420
<212> TYPE: PRT
<213> ORGANISM: Arabidopsis thaliana

<400> SEQUENCE: 4

```
Met Ala Ser Met Thr Gly Gly Gln Gln Met Gly Arg Asp Pro Ala Pro
 1               5                  10                  15

Arg Gln Ser Trp Asp Gly Pro Lys Pro Ile Ser Ile Val Gly Ser Thr
             20                  25                  30

Gly Ser Ile Gly Thr Gln Thr Leu Asp Ile Val Ala Glu Asn Pro Asp
         35                  40                  45

Lys Phe Arg Val Val Ala Leu Ala Ala Gly Ser Asn Val Thr Leu Leu
 50                  55                  60

Ala Asp Gln Val Arg Arg Phe Lys Pro Ala Leu Val Ala Val Arg Asn
 65                  70                  75                  80

Glu Ser Leu Ile Asn Glu Leu Lys Glu Ala Leu Ala Asp Leu Asp Tyr
                 85                  90                  95

Lys Leu Glu Ile Ile Pro Gly Glu Gln Gly Val Ile Glu Val Ala Arg
            100                 105                 110

His Pro Glu Ala Val Thr Val Val Thr Gly Ile Val Gly Cys Ala Gly
        115                 120                 125

Leu Lys Pro Thr Val Ala Ala Ile Glu Ala Gly Lys Asp Ile Ala Leu
130                 135                 140

Ala Asn Lys Glu Thr Leu Ile Ala Gly Gly Pro Phe Val Leu Pro Leu
145                 150                 155                 160

Ala Asn Lys His Asn Val Lys Ile Leu Pro Ala Asp Ser Glu His Ser
                165                 170                 175

Ala Ile Phe Gln Cys Ile Gln Gly Leu Pro Glu Gly Ala Leu Arg Lys
            180                 185                 190

Ile Ile Leu Thr Ala Ser Gly Gly Ala Phe Arg Asp Trp Pro Val Glu
        195                 200                 205

Lys Leu Lys Glu Val Lys Val Ala Asp Ala Leu Lys His Pro Asn Trp
210                 215                 220

Asn Met Gly Lys Lys Ile Thr Val Asp Ser Ala Thr Leu Phe Asn Lys
225                 230                 235                 240

Gly Leu Glu Val Ile Glu Ala His Tyr Leu Phe Gly Ala Glu Tyr Asp
                245                 250                 255

Asp Ile Glu Ile Val Ile His Pro Gln Ser Ile Ile His Ser Met Ile
            260                 265                 270

Glu Thr Gln Asp Ser Ser Val Leu Ala Gln Leu Gly Trp Pro Asp Met
        275                 280                 285

Arg Leu Pro Ile Leu Tyr Thr Met Ser Trp Pro Asp Arg Val Pro Cys
    290                 295                 300

Ser Glu Val Thr Trp Pro Arg Leu Asp Leu Cys Lys Leu Gly Ser Leu
305                 310                 315                 320

Thr Phe Lys Lys Pro Asp Asn Val Lys Tyr Pro Ser Met Asp Leu Ala
                325                 330                 335
```

-continued

```
Tyr Ala Ala Gly Arg Ala Gly Gly Thr Met Thr Gly Val Leu Ser Ala
            340             345             350

Ala Asn Glu Lys Ala Val Glu Met Phe Ile Asp Glu Lys Ile Ser Tyr
        355             360             365

Leu Asp Ile Phe Lys Val Val Glu Leu Thr Cys Asp Lys His Arg Asn
        370             375             380

Glu Leu Val Thr Ser Pro Ser Leu Glu Glu Ile Val His Tyr Asp Leu
385             390             395             400

Trp Ala Arg Glu Tyr Ala Ala Asn Val Gln Leu Ser Ser Gly Ala Arg
                405             410             415

Pro Val His Ala
            420
```